(12) United States Patent
Schesny et al.

(10) Patent No.: US 11,927,597 B2
(45) Date of Patent: Mar. 12, 2024

(54) LABORATORY SAMPLE VESSEL DISTRIBUTION SYSTEM, METHOD FOR OPERATING, AND IN-VITRO DIAGNOSTIC SYSTEM

(71) Applicant: Roche Diagnostics Operations, Inc., Indianapolis, IN (US)

(72) Inventors: Andreas Schesny, Stuttgart (DE); Vladimirs Leontjevs, Esslingen (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 418 days.

(21) Appl. No.: 17/232,290

(22) Filed: Apr. 16, 2021

(65) Prior Publication Data

US 2021/0333297 A1    Oct. 28, 2021

(30) Foreign Application Priority Data

Apr. 22, 2020 (EP) ..................................... 20170823

(51) Int. Cl.
*G01N 35/00* (2006.01)
*B01L 9/00* (2006.01)
(Continued)

(52) U.S. Cl.
CPC .......... *G01N 35/00584* (2013.01); *B01L 9/00* (2013.01); *B01L 9/06* (2013.01);
(Continued)

(58) Field of Classification Search
CPC ............. G01N 35/00584; G01N 21/59; G01N 33/487; G01N 35/00; G01N 35/0099;
(Continued)

(56) References Cited

U.S. PATENT DOCUMENTS 5,674,454 A    10/1997    Karl et al.
2009/0295262 A1    12/2009    Ward et al.
(Continued)

FOREIGN PATENT DOCUMENTS

CN    102438484 A    5/2012
CN    203083855 U    7/2013
(Continued)

OTHER PUBLICATIONS

European Search Report dated Sep. 17, 2020, in EP Application No. 20170823.7, 2 pp.
(Continued)

*Primary Examiner* — Benjamin R Schmitt
(74) *Attorney, Agent, or Firm* — Thomas E. Lees, LLC (57) ABSTRACT

A laboratory sample vessel distribution system is presented. The system comprises a cabinet, sample vessel carriers for receiving sample vessels, and a cabinet drawer for receiving a sample vessel carrier. The drawer is locatable in different positions: closed, opened, and fully opened. An actuator moves the sample vessels and the sample vessel carriers between different locations. An actuator driver drives the actuator and applies a first mode of operation with a first speed and a second mode of operation with a second reduced speed compared to the first speed. A sensor device detects between opened and closed positions and provides position signals. A control device is connected to the actuator driver and the sensor device. The control device provides control signals to the actuator driver instructing the actuator driver to apply either the first mode, if in the closed position, or the second mode, if in the opened position.

14 Claims, 6 Drawing Sheets

(51) Int. Cl.
  *B01L 9/06* (2006.01)
  *B25B 11/00* (2006.01)
  *G01N 21/59* (2006.01)
  *G01N 33/487* (2006.01)
  *G01N 35/04* (2006.01)

(52) U.S. Cl.
  CPC .............. *B25B 11/00* (2013.01); *G01N 21/59* (2013.01); *G01N 33/487* (2013.01); *G01N 35/00* (2013.01); *G01N 35/0099* (2013.01); *B01L 2200/085* (2013.01); *B01L 2200/18* (2013.01); *B01L 2300/04* (2013.01); *B01L 2300/0663* (2013.01); *G01N 2035/00306* (2013.01); *G01N 2035/00316* (2013.01); *G01N 2035/0491* (2013.01); *G01N 2035/0498* (2013.01)

(58) Field of Classification Search
  CPC .......... G01N 2035/00306; G01N 2035/00316; G01N 2035/0491; G01N 2035/0498; B01L 9/00; B01L 9/06; B01L 2200/085; B01L 2200/18; B01L 2300/04; B01L 2300/0663; B25B 11/00
  See application file for complete search history.

(56) References Cited

U.S. PATENT DOCUMENTS

| | | |
|---|---|---|
| 2013/0320832 A1 | 12/2013 | Ward et al. |
| 2017/0269114 A1 | 9/2017 | Bryant et al. |

FOREIGN PATENT DOCUMENTS

| | | |
|---|---|---|
| CN | 206161516 U | 5/2017 |
| CN | 108686729 A | 10/2018 |
| DE | 202012010656 | 1/2013 |
| EP | 3388840 A1 | 10/2018 |
| JP | 3181083 | 1/2013 |
| WO | 2004/034185 A2 | 4/2004 |
| WO | 2013/035471 A1 | 3/2013 |
| WO | 2016/133926 A1 | 8/2016 |
| WO | 2017/163586 A1 | 9/2017 |
| WO | 2019054002 A1 | 3/2019 |

OTHER PUBLICATIONS

Chinese first Office action and search report for Chinese Patent Application No. 202110438777.6; China National Intellectual Property Administration; Beijing, China; dated Jan. 10, 2024.

LABORATORY SAMPLE VESSEL DISTRIBUTION SYSTEM, METHOD FOR OPERATING, AND IN-VITRO DIAGNOSTIC SYSTEM

CROSS-REFERENCE TO RELATED APPLICATIONS

This application claims priority to EP 20170823.7, filed Apr. 22, 2020, which is hereby incorporated by reference.

BACKGROUND

The present disclosure generally relates to a laboratory sample vessel distribution system, a method for operating a laboratory sample vessel distribution system, and an in-vitro diagnostic system for determining a sample of a bodily fluid.

Such technology is applied for determining samples of a bodily fluid, wherein the samples are received in sample vessels or containers, which are processed in an in-vitro diagnostic system. The sample vessels are handled by a laboratory sample vessel distribution system, for example for locating the sample vessel in sample vessel carriers and for picking up the sample vessels from the sample vessel carriers.

In the in-vitro diagnostic system, the sample vessels are moved along a line of processing for processing, wherein the sample vessels and/or sample vessel carriers are moved by a transporting device having one or more actuators and actuator drivers or driving devices for driving the actuator(s). For example, the sample vessels may be moved or relocated from a first working station to a second working station provided in the line of processing in the in-vitro diagnostic system. The working stations may also be referred to as working location.

Therefore, there is a need for a laboratory sample vessel distribution system and a method for operating a laboratory sample vessel distribution system, which allow for safe operation, specifically, for protecting users interacting with the laboratory sample vessel distribution system in operation.

SUMMARY

According to the present disclosure, a laboratory sample vessel distribution system is presented. The laboratory sample vessel distribution system can comprise a cabinet having an interior space covered by cabinet walls, a plurality of sample vessel carriers having a plurality of support mounts each configured to detachably receive a sample vessel and a cabinet drawer configured to receive at least one sample vessel carrier from the plurality of sample vessel carriers. The cabinet drawer can be locatable in different position selected from the following: a closed position, in which a drawer opening assigned to the cabinet drawer is closed by a front panel of the cabinet drawer, an opened position, in which the drawer opening is open at least partially giving a user access to the interior space of the cabinet through the drawer opening, and a fully opened position, in which the drawer opening is closed by a back panel of the cabinet drawer. The laboratory sample vessel distribution system can also comprise an actuator provided in the interior space and configured to handle at least one of the sample vessels and the sample vessel carriers by moving the sample vessels and the sample vessel carriers between different locations, an actuator driver configured to drive the actuator and to apply a first mode of operation moving the actuator with a first speed of movement and to apply a second mode of operation moving the actuator with a second speed of movement being a reduced speed of movement compared to the first speed of movement, a sensor device assigned to the cabinet drawer and configured to detect a present drawer position of the cabinet drawer, the present drawer position being selected from the closed position and the opened position of the cabinet drawer, and to provide drawer position signals indicative of the present position of the cabinet drawer, and a control device connected to the actuator driver and to the sensor device for receiving the drawer position signals, the control device being configured to provide, in response to the drawer position signals, control signals to the actuator driver instructing the actuator driver to apply one of the first mode of operation, if the drawer position signals indicate the closed position and the second mode of operation, if the drawer position signals indicate the opened position.

Accordingly, it is a feature of the embodiments of the present disclosure to provide a laboratory sample vessel distribution system and a method for operating a laboratory sample vessel distribution system, which allow for safe operation, specifically, for protecting users interacting with the laboratory sample vessel distribution system in operation. Other features of the embodiments of the present disclosure will be apparent in light of the description of the disclosure embodied herein.

BRIEF DESCRIPTION OF THE SEVERAL VIEWS OF THE DRAWINGS

The following detailed description of specific embodiments of the present disclosure can be best understood when read in conjunction with the following drawings, where like structure is indicated with like reference numerals and in which.

DETAILED DESCRIPTION

In the following detailed description of the embodiments, reference is made to the accompanying drawings that form a part hereof, and in which are shown by way of illustration, and not by way of limitation, specific embodiments in which the disclosure may be practiced. It is to be understood that other embodiments may be utilized and that logical, mechanical and electrical changes may be made without departing from the spirit and scope of the present disclosure.

A laboratory sample vessel distribution system is provided. The laboratory sample vessel distribution system can comprise a cabinet having a interior space covered by cabinet walls, a plurality of sample vessel carriers having a plurality of support mounts each configured to detachably receive a sample vessel, and a cabinet drawer configured to receive at least one sample vessel carrier from the plurality of sample vessel carriers. The cabinet drawer can be locatable in different position selected from the following: a closed position, in which a drawer opening assigned to the cabinet drawer is closed by a front panel of the cabinet drawer; an opened position, in which the drawer opening is open at least partially, thereby, giving a user access to the interior space of the cabinet through the drawer opening; and a fully opened position, in which the drawer opening is closed by a back panel of the cabinet drawer. The laboratory sample vessel distribution system can further comprise an actuator provided in the interior space and configured to handle at least one of the sample vessels and the sample vessel carriers by moving the sample vessels and the sample vessel carriers, respectively, between different locations and an actuator driver configured to drive the actuator and to apply a first mode of operation, thereby, moving the actuator with a first speed of movement; and apply a second mode of operation, thereby, moving the actuator with a second speed of movement being a reduced speed of movement compared to the first speed of movement. Further, a sensor device can be assigned to the cabinet drawer and can be configured to detect a present drawer position of the cabinet drawer, the present drawer position being selected from the closed position, and the opened position of the cabinet drawer; and provide drawer position signals indicative of the present position of the cabinet drawer. A control device can be connected to the actuator driver and to the sensor device for receiving the drawer position signals, the control device being configured to provide, in response to the drawer position signals, control signals to the actuator driver instructing the actuator driver to apply one of the first mode of operation, if the drawer position signals indicate the closed position, and the second mode of operation, if the drawer position signals indicate the opened position.

A method for operating a laboratory sample vessel distribution system is provided. The system can comprise a cabinet having an interior space covered by cabinet walls, a plurality of sample vessel carriers having a plurality of support mounts each configured to detachably receive a sample vessel, and a cabinet drawer configured to receive at least one sample vessel carrier from the plurality of sample vessel carriers. The cabinet drawers can be locatable in different positions selected from the following: a closed position, in which a drawer opening assigned to the cabinet drawer is closed by a front panel of the cabinet drawer; an opened position, in which the drawer opening is open at least partially, thereby, giving a user access to the interior space of the cabinet through the drawer opening; and a fully opened position, in which the drawer opening is closed by a back panel of the cabinet drawer. The laboratory sample vessel distribution system can further comprise an actuator provided in the interior space and configured to handle at least one of the sample vessels and the sample vessel carriers by moving the sample vessels and the sample vessel carriers, respectively, between different locations. The method can comprise applying, by an actuator driver, a first mode of operation, thereby, moving the actuator with a first speed of movement; applying, by the actuator driver a second mode of operation, thereby, moving the actuator with a second speed of movement, the second speed of movement being a reduced speed of movement compared to the first speed of movement; detecting, by a sensor device assigned to the cabinet drawer, a present drawer position of the cabinet drawer, the present drawer position being selected from the closed position, and the opened position of the cabinet drawer; providing, by the sensor device, drawer position signals indicative of the present position of the cabinet drawer; and receiving the position signals by a control device connected to the sensor device and the actuator driver. The method can further comprise providing, by the control device in response to the drawer position signals, control signals to the actuator driver instructing the actuator driver to apply one of the first mode of operation, if the drawer position signals indicate the closed position, and the second mode of operation, if the drawer position signals indicate the opened position.

In response to detecting the opened position for the cabinet drawer which provides for the drawer opening being also open, the actuator can be moved with only reduced speed of movement (second mode of operation) compared to the first mode of operation applied before when the cabinet drawer is in the closed position. Movement with reduced speed can reduce likelihood for the user getting in conflict with the movement of the actuator or some sample vessel/sample vessel carrier moved for relocation by the actuator inside the cabinet. Likelihood for any collision of the user with some moving equipment can be limited or excluded.

The speed of movement can be changed for at least one of the sample vessel(s) and sample vessel carrier(s) carried or hold by or fixed to the actuator by changing speed of movement for the actuator, for example, some element or module holding or supporting the sample vessel and/or sample vessel carrier.

The speed of movement can be lowered in response to detecting the opened position of the drawer and can be capped at the reduced level (second speed of movement) for the time the opened position is detected by the sensor device. The laboratory sample vessel distribution system may switch back to applying the first mode of operation in response to detecting at least one of the closed position and the fully opened position after for some time the opened position was detected causing application of the second mode of operation.

One or more additional sensor devices can also be assigned to the cabinet drawer (and/or dome additional cabinet drawer) may be provided, the one or more additional sensor devices detecting sensor signals indicative of the cabinet drawer being in one of the closed position, the opened position and the fully the opened position.

In the second mode of operation, the second speed of movement providing a reduced or lowered level of speed compared to the first speed of movement may be applied to one or more driving elements such as motor devices of the actuator driver.

Another mode of operation which may also be referred to as third or hazard mode of operation may be applied if some hazard is detected by a hazard sensor device, the other mode of operation providing for a stop of the movement for the actuator. For example, a hazard signal may be provided by the hazard sensor device if some body part of the user is detected being too close to an actuator within the working space. By stopping movement of the sample vessel in response to the hazard signal, collision between the body part and the moving sample vessel can be avoided.

In addition to the drawer, one or more further drawers may be provided which may be operated as it is described for the drawer.

The sample vessel carrier may be permanently fixed to the cabinet drawer or may be detachably received in the cabinet drawer. If the sample vessel carrier is detachably provided in the cabinet drawer, it may be taken out and moved around in the interior space of the cabinet by an actuator for which speed of movement can be controlled as proposed.

For the laboratory sample vessel distribution system, the following may be provided: the sensor device can be configured to detect the present position of the cabinet drawer being the fully opened position and the control device can be configured to provide, in response to the drawer position signals, control signals to the actuator driver instructing the actuator driver to apply the first mode of operation, if the drawer position signals indicate the fully opened position. If the drawer is in the fully opened position, the drawer opening can be covered by the back panel of the cabinet drawer. The user may not have (accidently or purposefully) access to the interior space through the drawer opening. Thus, the first mode of operation can be applied.

The laboratory sample vessel distribution system may comprise a service detector device connected to the control device and configured to detect a service signal. The control device can be configured to provide, in response to the service signal and the drawer position signals indicating the opened position, control signals to the actuator driver instructing the actuator driver to: switch from the second mode of operation to the first mode of operation, if the second mode of operation is presently applied or continue with applying the first mode of operation, if the first mode of operation is presently applied.

Although the open position is detected for the cabinet drawer, there can be no switching to the second (reduced) speed of movement. Thus, there can be no reduction of the speed of movement for the actuator. If the second mode of operation is currently applied, it can be switched to the first mode of operation. The service detector device can provide the user or other staff member having the actuator (the sample vessel/sample vessel carrier) moved with the first speed of movement even the cabinet drawer is in the open position. Such mode of operation, for example, may be applied in case of maintenance or service work.

In still another embodiment, switching to the second (reduced) speed of movement may be applied in response to detecting the service signal, but the cabinet drawer being in one of the closed position and the fully opened position. Such mode of operation may be applied for maintenance or service work.

The cabinet may comprise a cabinet door relocatable between a closed-door position in which a door opening can be closed by the cabinet door and an opened door position in which the door opening can be open giving the user access to the interior space inside the cabinet through the door opening.

The laboratory sample vessel distribution system may comprise a door sensor device assigned to the cabinet door and connected to the control device. The door sensor device can be configured to detect a present door position of the cabinet door, the present door position being selected from the closed-door position and the opened door position; and to provide door position signals indicative of the present position of the cabinet door. The control device may be configured to provide, in response to the door position signals, control stop signals to the actuator driver instructing the actuator to stop. In response to the door position signals indicative of the cabinet door being in the opened position, the movement of the actuator can be stopped because of stopping the actuator driver.

In an embodiment, the cabinet door can be opened for giving to a user full access to a working area inside the cabinet where the actuator has access to sort the sample vessels into the different sample vessel carriers. If the cabinet door is opened, the system may stop moving of the sample vessels and/or the sample vessel carrier immediately to avoid personal damage to the user. Only some technicians may be allowed to drive the actuator in the second mode of operation with opened cabinet door, when the service signal is detected by the service detector device. Although the open position is detected for the cabinet door, there can be no switching to the second (reduced) speed of movement. Thus, there can be no reduction of the speed of movement for the actuator. If the second mode of operation is currently applied, it can be switched to the first mode of operation. The service detector device can provide the user or other staff member having the actuator (the sample vessel/sample vessel carrier) moved with the first speed of movement even the cabinet door is in the open position. Such mode of operation, for example, may be applied in case of maintenance or service work.

The actuator driver may be configured to conduct switching between applying the first mode of operation and applying the second mode of operation while the actuator is providing the sample vessels/the sample vessel carriers in one of the different locations.

The actuator driver may be configured to conduct switching between applying the first mode of operation and applying the second mode of operation while the actuator is moving the sample vessels/the sample vessel carriers between the different locations.

The actuator may comprise a vessel gripper. The actuator may be configured to locate the vessel gripper in a pick-up position, pick-up a sample vessel from a pick-up location by the vessel gripper, move the vessel gripper holding the sample vessel from the pick-up position to a drop position; and drop the sample vessel by the vessel gripper in a drop location. For moving the vessel gripper from the pick-up position to the drop position, the first speed of movement and the second speed of movement may be applied if the present position detected for the cabinet drawer by the sensor device is the closed position and the open position, respectively. For example, the vessel gripper may be moved between the pick-up position and the drop position by pivoting. The different modes of operation applying different speed of movement may also be applied to the vessel gripper without the vessel gripper actually holding a sample vessel, if the vessel gripper is moved between different locations while change of the position of the cabinet drawer is detected by the sensor device assigned to the cabinet drawer.

The actuator may comprise a conveyor device configured to transport at least one of the sample vessels and the sample vessel carriers. In response to detecting the different positions for the cabinet drawer, the speed of movement for the conveyor device can be changed.

The actuator driver may be further configured to move, in the second mode of operation, the actuator with a third speed of movement, the third speed of movement being a reduced speed of movement compared to the first speed of movement and being different from the second speed of movement. For different actuator drivers or driving devices different (reduced) speed of movement may be applied in response to detecting the opened position of the cabinet drawer. For example, the sample vessels/sample vessel carriers may be moved with a higher speed of movement in a subarea of the interior space not accessible by the user compared to a different subarea of the interior space actually accessible by the user if the cabinet drawer is open.

The actuator driver may be configured to gradually reduce the first speed of moving to the second speed of movement. Gradually reducing the speed level may be conducted by stepwise decreasing the speed from the first speed of movement to the second speed of movement. That can mean that there can be no abrupt or one-step reduction of the speed. Gradually changing the speed level may also be applied in case the speed of movement is increased after it has been reduced. Stepwise changing the speed may be conducted in dependence on a degree of opening of the cabinet drawer, which may be detected, for example, by detecting a distance of linear movement for the cabinet drawer moving from the closed position to the opened position. Alternatively, the speed may be changed between the first and the second speed of movement in a single step, thereby, abruptly reducing/increasing speed of movement for the sample vessel.

The moving of the sample vessels by one of more actuators may comprise moving the sample vessels between working stations from a plurality of working stations provided in a line of processing inside the cabinet. The different working stations, for example, may be provided for applying different steps in the process of determining and processing the sample received in the sample vessel or container. In an embodiment, in a first working station, a sample received in the sample vessel may be prepared. For preparation, the sample vessel may be provided to a vibrating device for vibrating the sample vessel, thereby, supporting mixing of sample components. In a second working station, which can be different from the first working station, the sample received in the sample vessel may be analyzed or determined. For example, an optical measurement such as transmission and/or absorbance measurement may be applied to the sample received in the sample vessel by an optical sample measurement module. Between the different working stations or locations, the sample vessel may be processed by moving the sample vessel by the transporting device. In addition, if necessary for processing, the sample vessel may be moved or relocated within a single working station. For example, the sample vessel may be lifted from a lower location to a higher location within a working station.

There may switching between the first mode of operation and the second mode of operation while a sample vessel is located or handled in a first working station of the line of processing. Change of the speed of movement can be conducted while the sample vessel is processed in the first working station.

Switching between the first mode of operation and the second mode of operation may be provided while the sample vessel or the sample vessel carrier is moved between different working stations in the line of processing. In this embodiment, the speed of movement can be changed while the sample vessel is relocated between different working stations. For example, speed of movement for a sample vessel carrier receiving the sample vessel may be changed while the sample vessel is transported or moved between consecutive working stations in the line of processing. The speed of movement for the sample vessel can be changed by changing speed of movement for the sample carrier.

The actuator driver may be configured to apply the first mode of operation in response to receiving a first driving voltage and to apply the second mode of operation in response to receiving a second driving voltage, which can be provided with a voltage level smaller than a voltage level of the first driving voltage. The reduced (second) speed of movement can be caused by reducing driving voltage level applied to the actuator driver driving the actuator. For example, speed of a motor (rotation) of the actuator driver may be reduced in response to lowering the driving voltage. Alternatively, other measures for changing speed of movement may be applied while a voltage level applied to the actuator driver can be kept essentially constant. For example, some mechanical or magnetic braking device may be provided.

In an embodiment, a voltage level of the first driving voltage can be gradually reduced to a voltage level of the second driving voltage. Gradually reducing the voltage level may be conducted by stepwise decreasing the voltage level from the first driving voltage to the second driving voltage. That can means that there can be no abrupt or one-step reduction of the voltage level. Gradually changing the voltage speed level may also be applied in case the driving voltage level is increased after it has been reduced. Stepwise changing the voltage level may be conducted in dependence on a degree of opening of the cabinet drawer, which may be detected, for example, by detecting a distance of linear movement for the cabinet drawer moving from the closed position to the opened position. Alternatively, the voltage level of the driving voltage may be changed between the first and the second driving voltage in a single step, thereby, abruptly reducing/increasing speed of movement for the sample vessel.

With respect to at least one of the method for operating a laboratory sample vessel distribution system and the in-vitro diagnostic system, the embodiments referred to above may apply mutatis mutandis.

A transporting device of the in-vitro diagnostics system may comprise at least one of the vessel gripper and the conveyor device. Such components or modules of the transporting device can be configured to be operated by both applying the first driving voltage and applying the second driving voltage.

Figure 1:
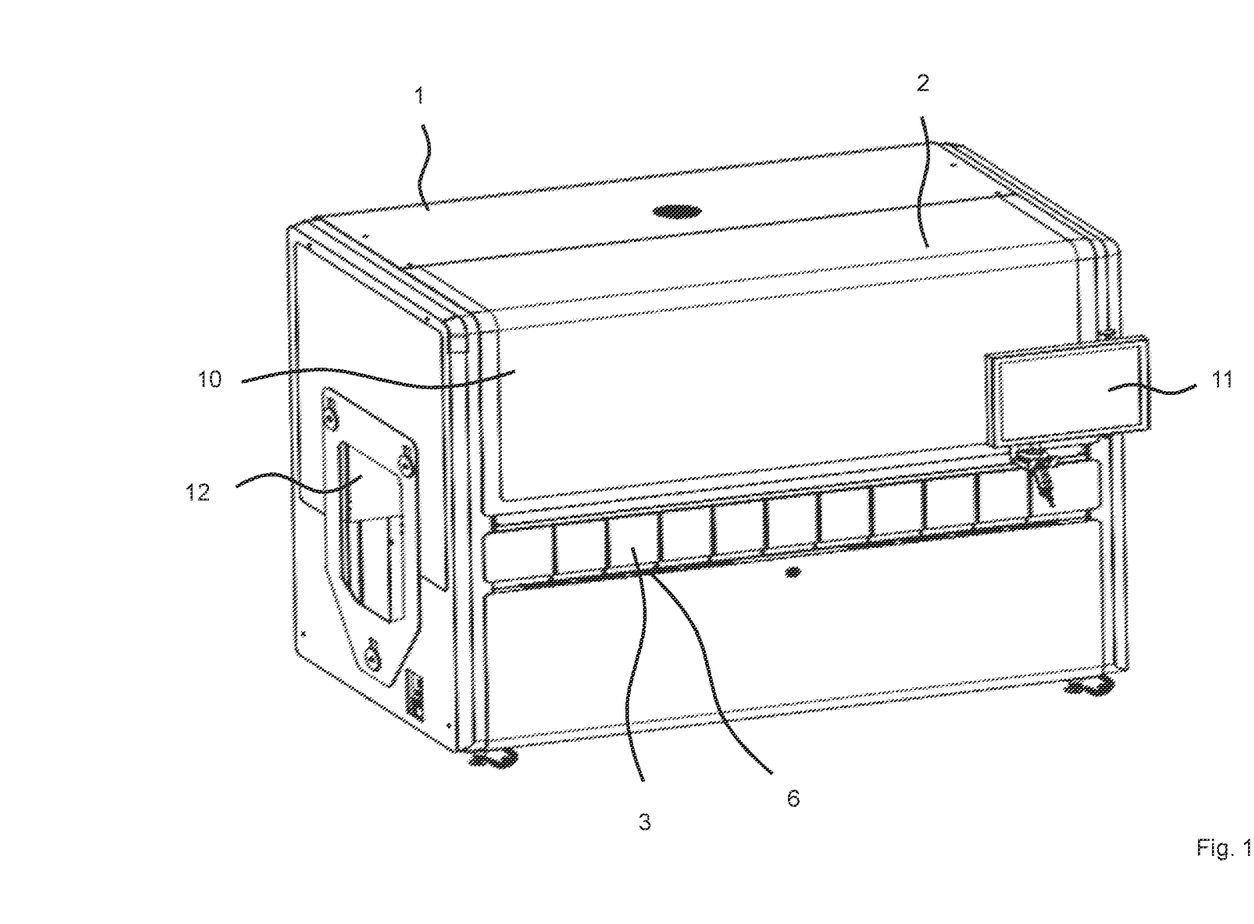
FIG. 1 illustrates a schematic representation of a cabinet of a laboratory sample vessel distribution system according to an embodiment of the present disclosure.
Figure 2:
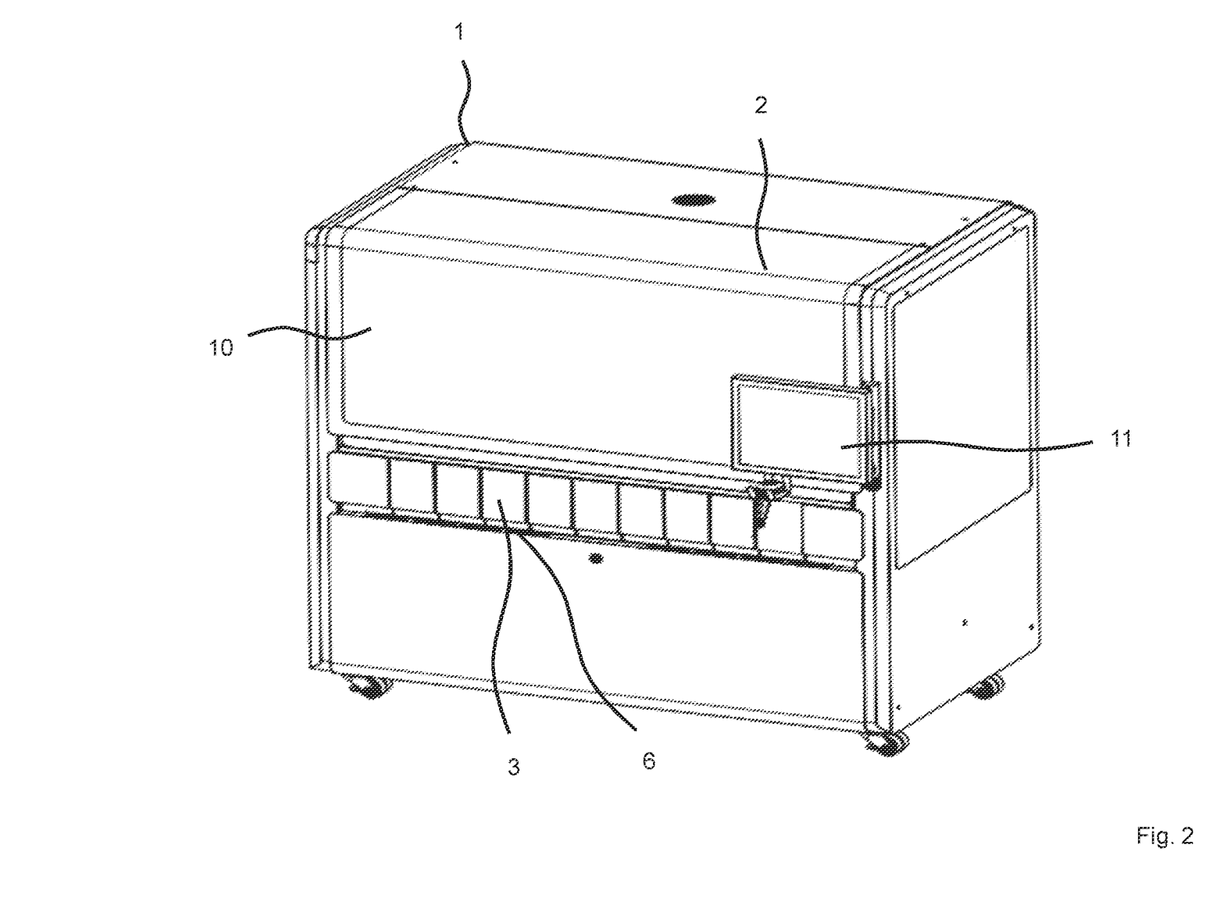
FIG. 2 illustrates another schematic representation of the cabinet FIG. 1 according to an embodiment of the present disclosure.

FIGS. 1 and 2 show a schematic representation of a cabinet 1 of a laboratory sample vessel distribution system which, for example, may be provided in an in-vitro diagnostic system configured to determine a sample of a bodily fluid. Within the cabinet 1, an interior space 2 can be provided which may also be referred to as working space.

Figure 3:
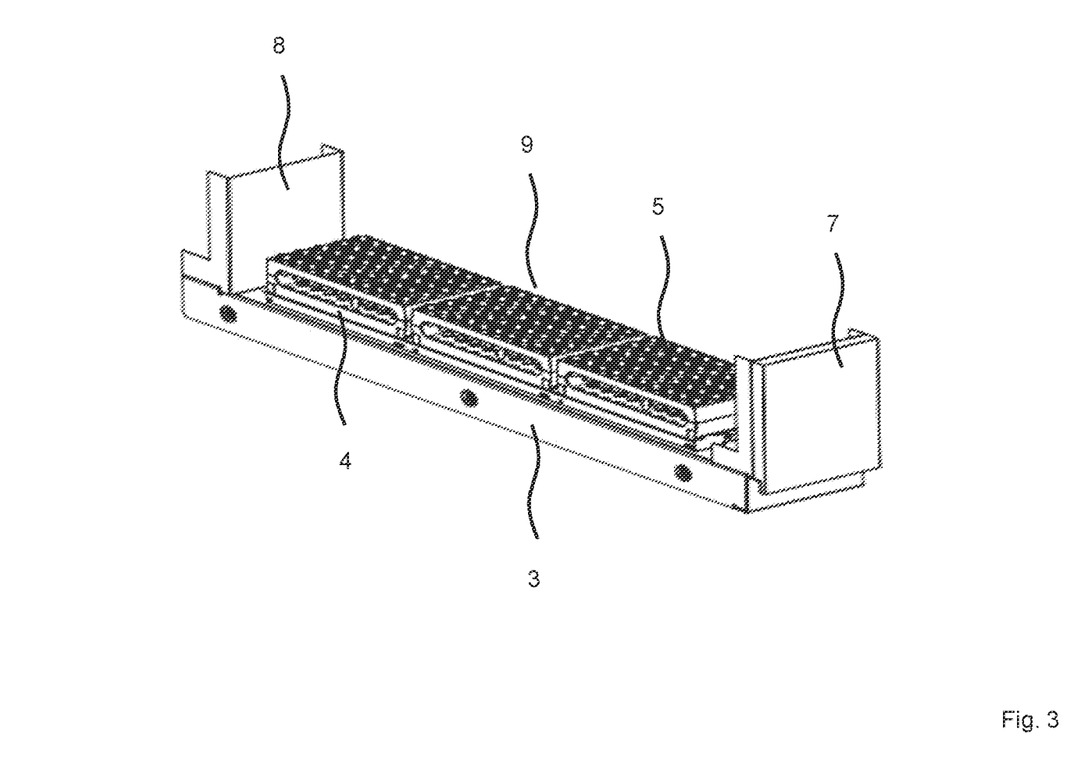
FIG. 3 illustrates a schematic representation of a cabinet drawer loaded with sample vessel carriers according to an embodiment of the present disclosure.
Figure 4:
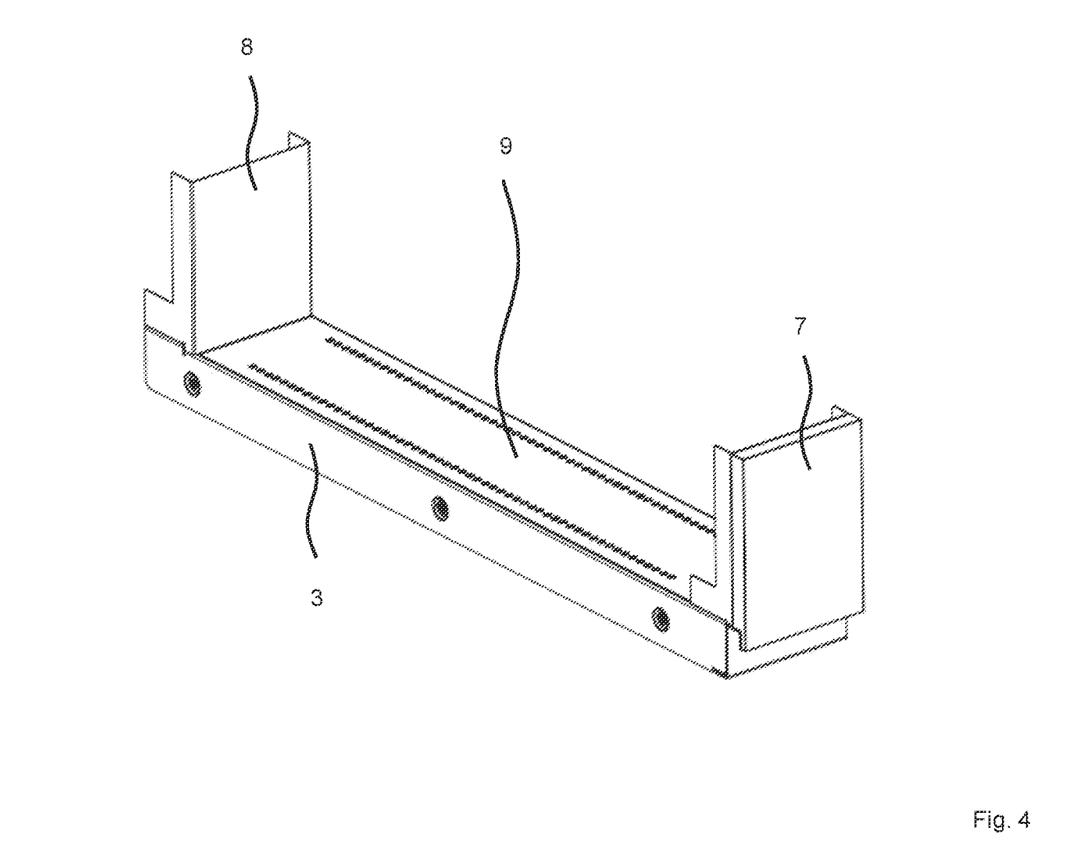
FIG. 4 illustrates a schematic representation of the cabinet drawer from FIG. 3 without sample vessel carriers according to an embodiment of the present disclosure.

FIGS. 3 and 4 show a schematic representation of a cabinet drawer 3 loaded with sample vessel carriers 4 receiving sample vessels 5 and a schematic representation of the cabinet drawer 3 without sample vessel carriers 4, respectively. The cabinet drawer 3 is to be received in a drawer opening 6 provided in the cabinet 1 (see FIGS. 1 and 2). The cabinet drawer 3 can comprise a front panel 7 and a back panel 8 providing a front cover and a back cover, respectively, for a space 9 of the cabinet drawer 3 for receiving the sample vessel carriers 4.

Referring to FIGS. 1 and 2, if the cabinet drawer 3 is in a closed position, the drawer opening 6 can be (fully) covered or closed by the front panel 7. Similarly, if the cabinet drawer 3 is in a fully opened position (not shown), the drawer opening 6 can be (fully) covered or closed by the back panel 8. Thus, in case the cabinet drawer 3 is located in one of the closed position and the fully opened position, a user operating or interacting with the laboratory sample vessel distribution system may not have access to the interior space 3 within the cabinet 1 through the drawer opening 6 (accidently or purposefully).

Contrary, in case the cabinet drawer 3 is in an opened position in which the cabinet drawer 3 is not fully, but partially pulled out, the drawer opening 6 may not be covered or closed by either the front panel 7 or the back panel 8. The drawer opening 6 being at least in part open can give the user access to the interior space 2.

For the cabinet 1, there can be a plurality of separated drawer openings 6 each receiving one or more cabinet drawers 3.

The cabinet 1 can be provided with a cabinet door 10 relocatable between a closed position (shown in FIGS. 1 and 2) and an open position (not shown) by lifting up the cabinet door 10. If the cabinet door 10 is in the open positon, the user can have access to the interior space 2. In the closed position, the interior space 2 can be fully covered.

A display panel 11 can provide for a user interface.

In the interior space 2, the sample vessel carriers 4 may be picked up from the cabinet drawer 3 if the cabinet drawer 3 is in the closed position (see FIGS. 1 and 2), for example, for placing the sample vessel carriers 4 on a transport belt or robot configured to transport (by movement) the sample vessel carriers 4 to some working station (not shown) inside or outside of the cabinet 1. Transporting the sample vessel carriers 4 outside the cabinet may be conducted through a wall opening 12.

Further, in the interior space 2, the sample vessels 5 may be picked up from the sample vessel carriers 4 and relocated. For example, a sample vessel 5 may be moved to some working station in a line of sample processing (not shown).

For processing, the sample vessels 5 receiving the sample of the bodily fluid to be analyzed may be moved in the line of processing by one or more actuators, which may comprise, for example, at least one of a sample vessel gripper, a conveyor device, and a gantry robot. Such actuators of different types applied in the laboratory sample vessel distribution system are known. For example, the gantry robot can allow for linear movement along three-principle axis. Gantry robots may also be referred to as Cartesian coordinate robots and are known as such.

In the line of processing the sample vessels 5 containing a sample to be determined can be moved to a plurality of working stations. The different working stations may be provided for applying different steps in the process of determining and processing the sample received in the sample vessels or containers 5. For example, in a first working station, the sample received in one of the sample vessels 5 may be prepared. For preparation, the sample vessel may be provided to a vibrating device for vibrating the sample vessel, thereby, supporting mixing of sample components. In a second working station, which can be different for the first working station, the sample received in the sample vessel may be analyzed or determined. In one embodiment, an optical measurement such as transmission and/or absorbance measurement may be applied to the sample received in the sample vessel by an optical sample measurement module (not shown). Between the different working stations or locations, the sample vessels 5 may be processed by moving the sample vessels 5 by the actuator(s).

Figure 5:
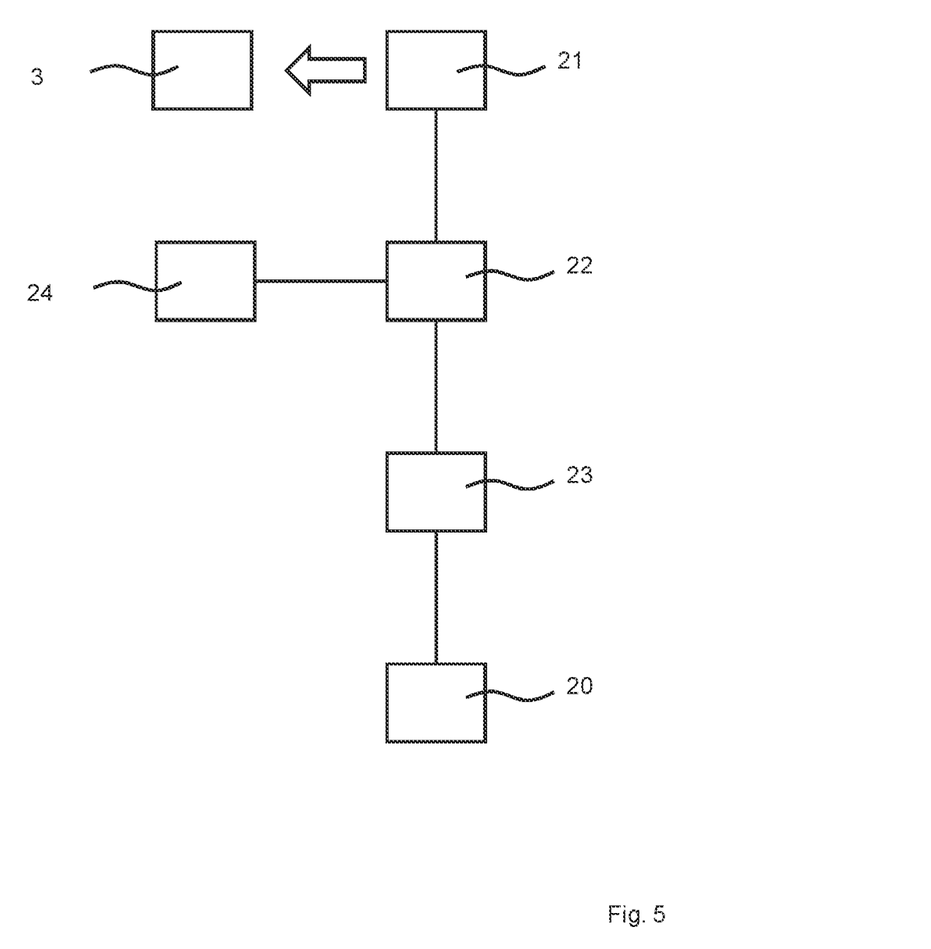
FIG. 5 illustrates a schematic representation of an arrangement for controlling operation of an actuator in the laboratory sample vessel distribution system according to an embodiment of the present disclosure.

FIG. 5 shows a schematic representation of an arrangement for controlling operation of an actuator 20 in the laboratory sample vessel distribution system provided with the cabinet 1. A sensor device 21 can be assigned to the cabinet drawer 3 for detecting a current or present position of the cabinet drawer 3, the current position being selected from the following: a closed position, in which the drawer opening 6 assigned to the cabinet drawer 3 is closed by the front panel 7 of the cabinet drawer 3; an opened position, in which the drawer opening 6 is open at least partially, thereby, giving the user access to the interior space 2 of the cabinet 1 through the drawer opening 6; and a fully opened position, in which the drawer opening 6 is closed by the back panel 7 of the cabinet drawer 3. The sensor device may be provided with one or more sensor elements assigned to the cabinet drawer 3. For example, the sensor device 21 may comprise a proximity sensor and/or an optical sensor (light gate).

The sensor device 21 can be connected to a control device 22 configured to receive the sensor signals indicative of the current position of the cabinet drawer 3 from the sensor device 21 and to generate, in dependence on the sensor signals, control signals for controlling operation of a actuator driver 23. The actuator driver 23 can be configured to drive the actuator 20 in response to the control signals received from the control device 22 for handling or moving at least one of the sample vessel carriers 4 and the sample vessels 5.

Further, a service detector device 24 can be connected to the control device 22. The service detector device 24 can be configured to receive user input and may be provided with a shutter or a touch sensitive element for user input.

Figure 6:
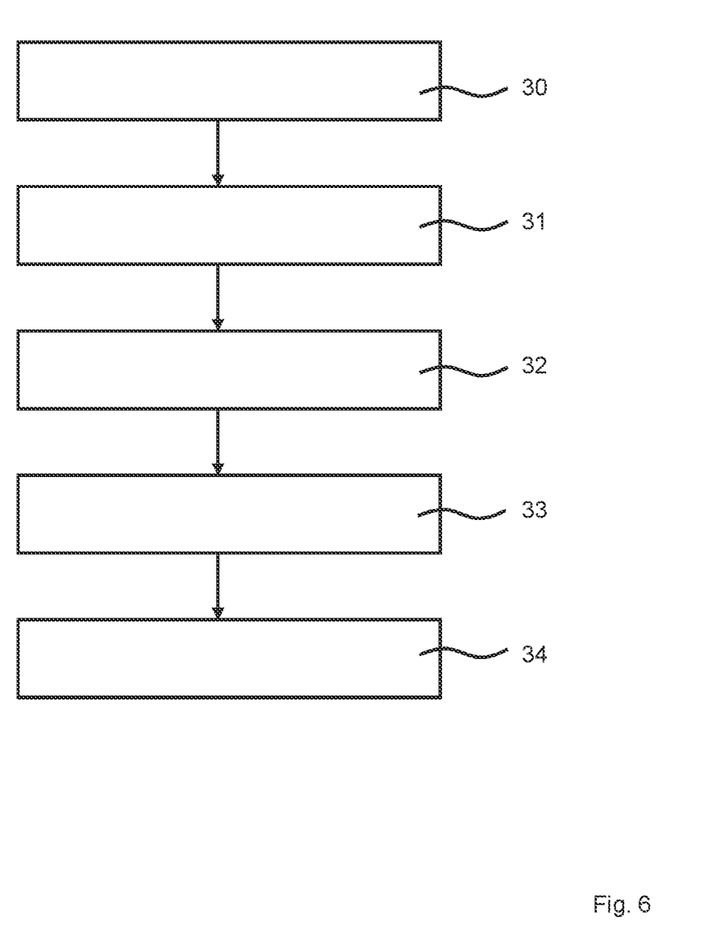
FIG. 6 illustrates a schematic block diagram for a method of safely operating a laboratory sample vessel distribution system in an in-vitro diagnostic system for determining a sample of a bodily fluid according to an embodiment of the present disclosure.

Referring to FIG. 6, a method for safely operating the laboratory sample vessel distribution system provided with the cabinet 1 may be applied as follows. In step 30, a first mode of operation can be conducted. A first driving voltage can be applied to the actuator driver 23 driving the actuator 20 for moving or handling at least one of the sample vessels 5 and the sample vessel carriers 4 within the interior space 2 of the cabinet 1. In the first mode of operation, the sample vessels 5 and/or the sample vessel carriers 4 can be moved with a first speed of movement by the actuator(s) 20. Such a first speed of movement can be conducted by applying a first driving voltage to the actuator driver 23 driving the actuator 20.

If in step 31, if the opened position is detected for the cabinet drawer 3 by the sensor device 21 assigned to the cabinet drawer 3, a second mode of operation can be applied in step 32. According to the second mode of operation, a second driving voltage can be applied to the actuator driver 23, the second driving voltage being reduced compared to the first driving voltage. In response to applying the second driving voltage, the sample vessels 5 and/or the sample vessel carriers 4 can be moved by the actuator 20 with a second speed of movement, which can be lower than the first speed of movement.

If in step 33, again, the closed position is detected for the cabinet drawer 3, the first mode of operation can be applied in step 34, thereby, moving the actuator 20 with the first speed of movement again. Alternatively, the fully opened position may be detected for the cabinet drawer 3, which can also cause applying the first mode of operation again In conclusion, depending on the cabinet drawer 3 being in one of the closed position, the opened position and the fully opened position, different driving voltage can be applied to the actuator driver 23, thereby, moving the actuator(s) 20 with different speed. Reducing the speed of movement in the opened position can avoid collision of a body part of the user with the moving actuator 20, some sample vessel 5, some sample vessel carrier 4 or some other moving element, if the user has access to the interior space 2 because of the drawer opening being open (not covered by one of the front panel 7 or the back panel 8). At least, it can reduce the impact damage to some negligible level.

The first speed of movement may be kept for or applied, even if the cabinet drawer 3 is detected to be in the opened position, if, in addition to the sensor signal detecting the position of the cabinet drawer 3, a service signal is received from the service detector device 25 which may be provided with a switch or a touch button for detecting user input, for example, on the display panel 11. Such mode of operation, namely moving the actuator 20 with the first speed of movement while the cabinet drawer 3 is in the opened position, may be applied for maintenance or service work.

In the case the cabinet door 10 is opened and usually the motor stops but can be work in second mode for maintenance. Switching from first to second mode of operation because of the cabinet drawer 3 being opened and not stopping the actuator 20 can have the advantage that a continuous workflow can be conducted. Thus, a user can exchange the sample vessel carriers 4 without stopping the workflow totally. If a full sample vessel carrier has to be taken away and some empty sample vessel carrier has to be put into the cabinet drawer 3, sorting of sample vessels between remaining sample vessels carriers can continue.

In an example, different DC voltage levels may be applied to the actuator driver(s) 20. For example, the first speed of movement may be provided in response to applying 42 VDC, while the second speed of movement can be provided in response to applying 12 VDC. In an example, one or more motors (driver devices) may be applied the different voltage level for controlling movement of the actuators with the different speed of movement.

There may be one or more additional sensor devices assigned to the interior space 2, the one or more sensor devices configured to detect, for example, presence of a body part of the user within the interior space 2. In response to such detection (e.g. hazard), movement of the actuator 20 may be stopped. While moving of at least one of the sample vessel carrier 4 and the sample vessels 5 cam be continued for both applying the first driving voltage and applying the second driving voltage, such processing (movement) can be prevented in response to detecting such hazard (e.g, body part of the user detected).

Depending on a plurality of detector signals, different modes of operation (speed of movement) may be applied (see Table 1).

TABLE 1

| Cabinet door opened | Cabinet drawer in opened position | Service signal | Main power fail detected | Emergency stop signal (hazard) | Error from safety system | Speed of movement |
|---|---|---|---|---|---|---|
| No | No | X | No | No | No | Full speed |
| Yes | X | Yes | No | No | No | Reduced speed |
| No | Yes | No | No | No | No | Reduced speed |
| Yes | X | No | No | No | No | Controlled stop |
| X | X | X | Yes | X | No | Controlled stop |
| X | X | X | X | Yes | No | Controlled stop |
| X | X | X | X | X | Yes | Controlled stop |

According to the above scenarios, the second mode of operation ("Reduced speed") can be applied if an opened position is detected for the cabinet drawer 3. The second mode of operation can also be applied if the following is detected a fully opened or closed position is detected for the cabinet drawer, and, in addition, a service signal is detected by the service detector device 25.

Different from the mode of operation identified in Table 1, lowering of the voltage level (second mode of operation—reducing speed of movement) may not be applied if, in addition to detecting the open position for the cabinet drawer 3, the service signal is detected.

It is noted that terms like "preferably," "commonly," and "typically" are not utilized herein to limit the scope of the claimed embodiments or to imply that certain features are critical, essential, or even important to the structure or function of the claimed embodiments. Rather, these terms are merely intended to highlight alternative or additional features that may or may not be utilized in a particular embodiment of the present disclosure.

Having described the present disclosure in detail and by reference to specific embodiments thereof, it will be apparent that modifications and variations are possible without departing from the scope of the disclosure defined in the appended claims. More specifically, although some aspects of the present disclosure are identified herein as preferred or particularly advantageous, it is contemplated that the present disclosure is not necessarily limited to these preferred aspects of the disclosure.

We claim:

1. A laboratory sample vessel distribution system, the laboratory sample vessel distribution system comprising:
 a cabinet having an interior space covered by cabinet walls;
 a plurality of sample vessel carriers having a plurality of support mounts each configured to detachably receive a sample vessel;
 a cabinet drawer configured to receive at least one sample vessel carrier from the plurality of sample vessel carriers, the cabinet drawer being locatable in different position selected from the following:
  a closed position, in which a drawer opening assigned to the cabinet drawer is closed by a front panel of the cabinet drawer,
  an opened position, in which the drawer opening is open at least partially giving a user access to the interior space of the cabinet through the drawer opening, and
  a fully opened position, in which the drawer opening is closed by a back panel of the cabinet drawer;
 an actuator provided in the interior space and configured to handle at least one of the sample vessels and the sample vessel carriers by moving the sample vessels and the sample vessel carriers between different locations;
 an actuator driver configured to drive the actuator and to apply a first mode of operation moving the actuator with a first speed of movement and to apply a second mode of operation moving the actuator with a second speed of movement being a reduced speed of movement compared to the first speed of movement;
 a sensor device assigned to the cabinet drawer and configured to detect a present drawer position of the cabinet drawer, the present drawer position being selected from the closed position and the opened position of the cabinet drawer, and to provide drawer position signals indicative of the present position of the cabinet drawer; and
 a control device connected to the actuator driver and to the sensor device for receiving the drawer position signals, the control device being configured to provide, in response to the drawer position signals, control signals to the actuator driver instructing the actuator driver to apply one of the first mode of operation, if the drawer position signals indicate the closed position and the second mode of operation, if the drawer position signals indicate the opened position.

2. The laboratory sample vessel distribution system of claim 1, wherein the sensor device is configured to detect the present position of the cabinet drawer being the fully opened position and the control device is configured to provide, in response to the drawer position signals, control signals to the actuator driver instructing the actuator driver to apply the first mode of operation, if the drawer position signals indicate the fully opened position.

3. The laboratory sample vessel distribution system of claim 1, further comprising,
a service detector device connected to the control device and configured to detect a service signal, wherein the control device is configured to provide, in response to the service signal and the drawer position signals indicating the opened position, control signals to the actuator driver instructing the actuator driver to switch from the second mode of operation to the first mode of operation, if the second mode of operation is presently applied, or to continue with applying the first mode of operation, if the first mode of operation is presently applied.

4. The laboratory sample vessel distribution system of claim 1, wherein the cabinet comprises a cabinet door relocatable between a closed door position in which a door opening is closed by the cabinet door and an opened door position in which the door opening is open giving the user access to the interior space of the cabinet through the door opening.

5. The laboratory sample vessel distribution system of claim 4, further comprising,
a door sensor device assigned to the cabinet door and connected to the control device, wherein the door sensor device is configured to detect a present door position of the cabinet door, the present door position being selected from closed and opened door position and to provide door position signals indicative of the present position of the cabinet door and wherein the control device is configured to provide, in response to the door position signals, control stop signals to the actuator driver instructing the actuator driver to stop.

6. The laboratory sample vessel distribution system of claim 1, wherein the actuator driver is configured to conduct switching between applying the first mode of operation and applying the second mode of operation while the actuator is providing the sample vessels/the sample vessel carriers in one of the different locations.

7. The laboratory sample vessel distribution system of claim 1, wherein the actuator driver is configured to conduct switching between applying the first mode of operation and applying the second mode of operation while the actuator is moving the sample vessels/the sample vessel carriers between the different locations.

8. The laboratory sample vessel distribution system of claim 1, wherein the actuator comprises a vessel gripper and is configured to locate the vessel gripper in a pick-up position, to pick-up a sample vessel from a pick-up location by the vessel gripper, to move the vessel gripper holding the sample vessel from the pick-up position to a drop position, and to drop the sample vessel by the vessel gripper in a drop location, wherein, for moving the vessel gripper from the pick-up position to the drop position, the first speed of movement and the second speed of movement is applied if the present position detected for the cabinet drawer by the sensor device is the closed position and the open position, respectively.

9. The laboratory sample vessel distribution system of claim 1, wherein the actuator comprises a conveyor device configured to transport at least one of the sample vessels and the sample vessel carriers.

10. The laboratory sample vessel distribution system of claim 1, wherein actuator driver is configured to move, in the second mode of operation, the actuator with a third speed of movement, the third speed of movement being a reduced speed of movement compared to the first speed of movement, and being different from the second speed of movement.

11. The laboratory sample vessel distribution system of claim 1, wherein the actuator driver is configured to gradually reduce the first speed of moving to the second speed of movement.

12. The laboratory sample vessel distribution system of claim 1, wherein the actuator driver is configured to apply the first mode of operation in response to receiving a first driving voltage and to apply the second mode of operation in response to receiving a second driving voltage which is provided with a voltage level smaller than a voltage level of the first driving voltage.

13. An in-vitro diagnostic system for determining a sample of a bodily fluid, the in-vitro system comprising:
a laboratory sample vessel distribution system of claim 1.

14. A method for operating a laboratory sample vessel distribution system, the system comprising a cabinet having an interior space covered by cabinet walls, a plurality of sample vessel carriers having a plurality of support mounts each configured to detachably receive a sample vessel, a cabinet drawer configured to receive at least one sample vessel carrier from the plurality of sample vessel carriers, the cabinet drawer being locatable in different positions selected from the following a closed position, in which a drawer opening assigned to the cabinet drawer is closed by a front panel of the cabinet drawer, an opened position, in which the drawer opening is open at least partially, thereby, giving a user access to the interior space of the cabinet through the drawer opening, and a fully opened position, in which the drawer opening is closed by a back panel of the cabinet drawer, and an actuator provided in the interior space and configured to handle at least one of the sample vessels and the sample vessel carriers by moving the sample vessels and the sample vessel carriers between different locations, the method comprising:
applying, by an actuator driver, a first mode of operation, thereby, moving the actuator with a first speed of movement;
applying, by the actuator driver, a second mode of operation, thereby, moving the actuator with a second speed of movement, the second speed of movement being a reduced speed of movement compared to the first speed of movement;
detecting, by a sensor device assigned to the cabinet drawer, a present drawer position of the cabinet drawer, the present drawer position being selected from the closed position, and the opened position of the cabinet drawer;
providing, by the sensor device, drawer position signals indicative of the present position of the cabinet drawer;
receiving the position signals by a control device connected to the sensor device and the actuator driver; and
providing, by the control device in response to the drawer position signals, control signals to the actuator driver instructing the actuator driver to apply one of the first mode of operation, if the drawer position signals indicate the closed position, and the second mode of operation, if the drawer position signals indicate the opened position.

* * * * *